Figure 1:
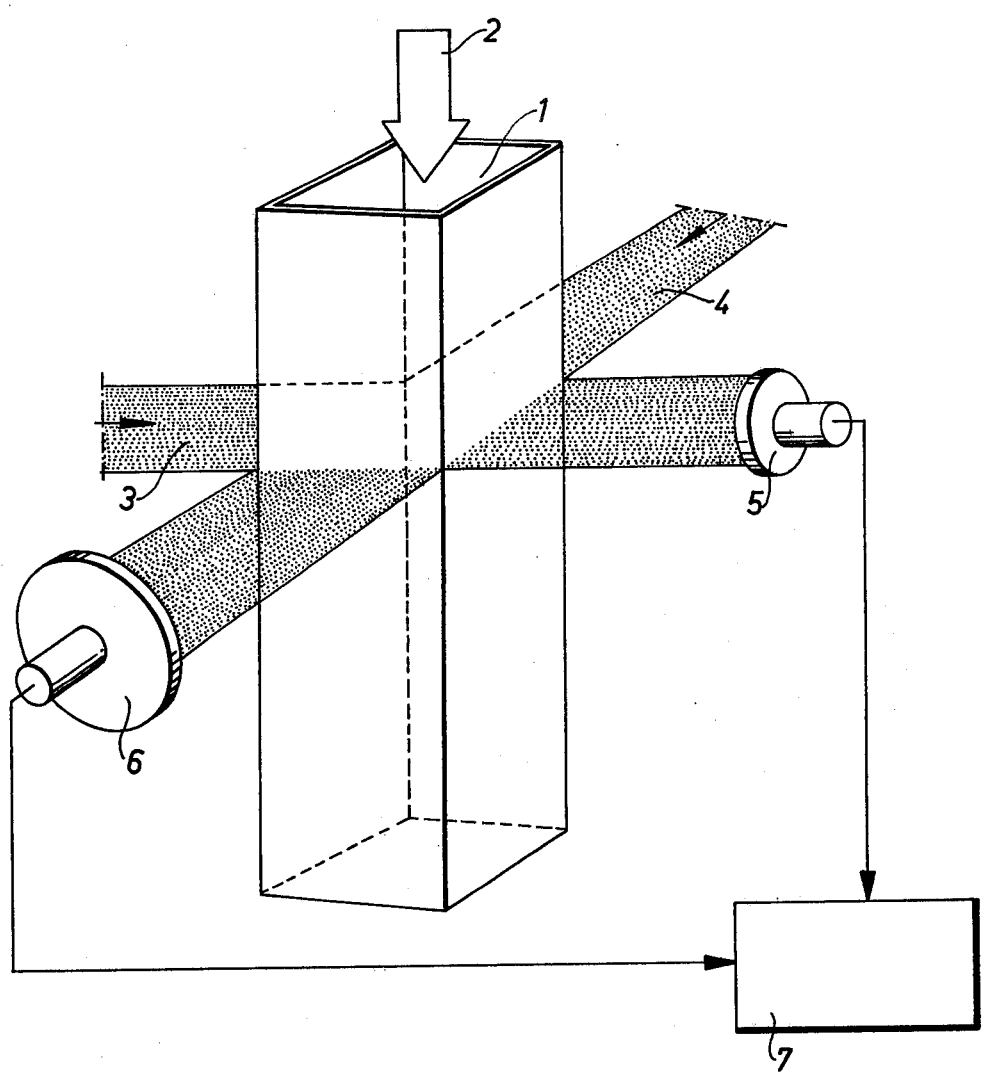

United States Patent [19]

Hill

[11] 4,066,492
[45] Jan. 3, 1978

[54] METHOD AND DEVICE FOR EXAMINING PULP FOR THE PRESENCE OF SHIVES

[75] Inventor: Jan Hill, Taby, Sweden

[73] Assignee: AB Tellusond, Stockholm, Sweden

[21] Appl. No.: 685,491

[22] Filed: May 12, 1976

[30] Foreign Application Priority Data

May 14, 1975 Sweden .................................. 7505538

[51] Int. Cl.[2] ...................... G01N 15/02; G01N 21/34
[52] U.S. Cl. .......................................... 162/49; 162/50; 162/263; 250/339; 356/51
[58] Field of Search ................. 162/DIG. 10, , 49, 50, 162/198, 263; 250/573, 339, 341; 356/208, 206, 102, 51; 209/111.5

[56] References Cited

U.S. PATENT DOCUMENTS

| | | |
|---|---|---|
| 3,498,719 | 3/1970 | Wing et al. ...................... 356/208 X |
| 3,518,003 | 6/1970 | Meyn ................................. 162/49 X |
| 3,652,850 | 3/1972 | Briggs ............................... 356/208 X |
| 3,724,957 | 4/1973 | Tamate et al. .................... 356/208 X |
| 3,823,320 | 7/1974 | Ledoux ............................. 356/102 |
| 3,879,129 | 4/1975 | Inoue ................................ 356/208 X |
| 3,980,517 | 9/1976 | MacTaggart ............. 162/DIG. 10 X |

OTHER PUBLICATIONS

Brecht et al., "Spot and Shive Counts in Halfstuffs and Whole Stuffs by Means of Optical Electronic Instrument," Papies 22, No. 10A, 784–792, 10–1968, Abstract 8656, ABIPC, vol. 39, No. 10, (Apr. 1969).

Johnsson, et al., "Determination of Dangerous Shives," Internatl. Mechanical Pulping Conference, 1973.

*Primary Examiner*—S. Leon Bashore
*Assistant Examiner*—Steve Alvo
*Attorney, Agent, or Firm*—Kenway & Jenney

[57] ABSTRACT

In a method for examining pulp for the presence of shives therein a suspension of the pulp is passed through a measuring duct with transparent walls and at least one beam of light having a wavelength within the intra-red range from 750 to 950 nm is directed through the measuring duct perpendicularly to the direction of flow of the pulp suspension therein. The intensity of the light beam after its passage through the measuring duct is measured by means of a photo detector and the output signal of the photo detector is analyzed with respect to amplitude variations therein. The measurement is independent and insensitive to the type of pulp.

3 Claims, 2 Drawing Figures

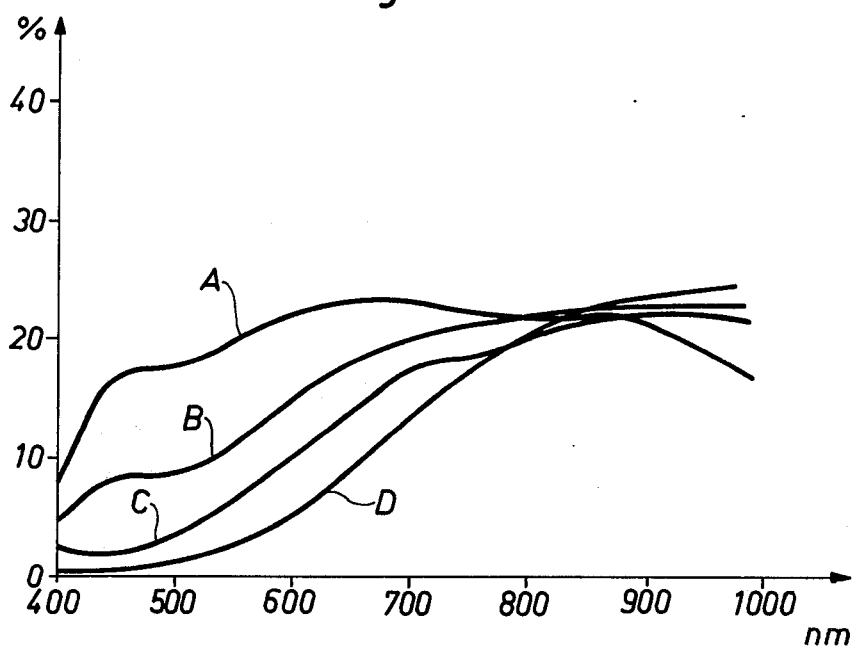

METHOD AND DEVICE FOR EXAMINING PULP FOR THE PRESENCE OF SHIVES

The present invention is related to a method and a device for testing and examining pulp for the presence of shives therein.

A "shive" is a larger fiber bundle consisting of two or more fibers which adhere to each other and which have not been completely separated from each other during the production of the pulp. The shives differ from the fibers in the pulp primarlily in that they have a larger cross-section dimension than the fibers and thus generally also a somewhat larger length in average than the fibers. Whereas the fibers generally have a cross-section dimension (thickness) of 10–16 μm the shives, or what is generally called shives, have a corresponding cross-section dimension from 80–150 μm and upwards. The lower limit for the cross-section dimension of what is called "shives" is often dependent on the capability of the available measuring apparatus of distinguishing between thin shives, i.e. shives having a comparatively small cross-section dimension, and fibers. The average length of the shives is generally 1.5 to 2 times larger than the average length of the fibers, but this value depends on the type of the pulp.

The presence of shives in a paper pulp is an important factor for the quality of the pulp. One reason for this is that each shive will cause a weak spot or an initiative to rupture in the paper web being manufactured from the pulp and therefore increase the risk of rupture of paper web during its manufacture. Further, a shive located in the surface of the manufactured paper will also impair the printing qualities of the paper, for instance in that the shive accepts and adsorbs the printing ink in a manner different from the surrounding paper or in that the shive comes loose from the paper surface during the printing process and possibly adheres to the printing form or printing plate. Consequently, it is of important interest to be able to examine pulp with respect to the presence of shives therein, the primary interest being to determine the total amount of shives in a given quantity of pulp but also to obtain information of the size or the size range of the shives present in the pulp.

A prior art method for examining paper pulp for the presence of shives therein comprises the steps of passing a suspension of the pulp through a measuring duct having transparent walls and directing a substantially parallel beam of light from a light source located at one side of the measuring duct through the measuring duct towards a photo detector located on the opposite side of the measuring duct in such a manner that the direction of the light beam is substantially perpendicular to the longitudinal direction of the measuring duct, i.e., to the direction of flow of the pulp suspension. A shive present in the pulp suspension will, when it passes through the light beam, give cause to a reduction in the intensity of the light received by the photo detector and thus to a corresponding reduction in the amplitude of the output signal of the photo detector. The magnitude of this reduction in intensity and amplitude, respectively, constitutes a measure of the cross-section dimension of the shives in a direction perpendicular to the light beam, whereas the duration of the reduction in intensity and amplitude, respectively, is a measure of the length of the shive, as the shives orient themselves in the pulp suspension flow with their longitudinal direction substantially coinciding with the direction of flow. By analyzing the output signal of the photo detector with respect to the amplitude variations in the signal it is consequently possible to obtain information on the presence of shives in the pulp. As the cross-section of a shive is often rectangular, i.e., the shive is thin and broad, it is the preferred practice to direct two light beams through the measuring duct at right angles to each other and in a common plane perpendicular to the longitudinal direction of the measuring duct. These two light beams are, after their passage through the measuring duct, received by two corresponding photo detectors and the output signals of these photo detectors are combined to a combined signal, which is subsequently analyzed, as mentioned above, with respect to the occurrence of amplitude variations therein caused by shives in the pulp.

It is self-evident that in a measuring process of this kind it is important that the result of the measurement is independent of and unaffected by the type of the pulp being examined, i.e., the production process and the degree of bleaching of the pulp. However, it has been found that such an insensitivity to the origin of the pulp is not normally achieved, as shives from different pulp production processes and with different degrees of bleaching of the pulp will display large differences in colouring.

The object of the present invention is therefore to provide an improved method in a corresponding improved device of the type mentioned in the foregoing for examining pulp with respect to the presence of shives therein, which gives measuring results that are independent of and insensitive to the origin of the pulp and thus of the shives.

According to the invention this is achieved in that light having a wavelength within the range from 750 to 950 nm is used. In view of the light sources available on the market one may preferably use luminiscence diodes having the wavelength 930 nm.

The invention is founded on the discovery that when using light within said wavelength range, i.e., mainly within the infra-red range, the reduction in intensity of the light beam caused by a given shive will be substantially independent of the origin of the shive, i.e., of the pulp production process and the degree of bleaching, and will consequently be dependent only of the size of the shive.

In the following the invention will be further described in more detail with reference to the accompanying drawings, in which FIG. 1 shows schematically a device for examining pulp with respect to the presence of shives therein, in which the method according to the invention is employed; and FIG. 2 is a graphic illustration of the transmission of a light beam passing through the measuring duct and affected by a shive as a function of the wavelength of the light and for shives of different origins.

FIG. 1 shows very schematically and only in principle a device for examining pulp for the presence of shives therein, comprising a measuring duct 1 with transparent walls, through which a flow of a suspension of the pulp to be examined is passed, as indicated by an arrow 2. From light sources with associated optical systems (not shown in the drawings) two mutually perpendicular light beams 3 and 4 are directed thorugh the measuring duct 1 in a common plane perpendicular to the longitudinal direction of the measuring duct 1. Each of these light beams 3 and 4 consists of substantially parallel light rays and is shaped by the optical system associated with the light source so as to have a comparatively thin rectangular cross-section so that the light beam has substantially the form of a thin ribbon disposed in the plane perpendicular to the longitudinal axis of the measuring duct 1. After their passage through the measuring duct 1 the two light beams 3 and 4 are received by photo detectors 5 and 6, respectively, which consequently will provide output signals proportional to the intensities of the light beams 3 an 4, respectively, after their passage through the measuring duct 1 and the flow of pulp suspension present in the measuring duct. It will be appreciated that if a shive is present in the pulp suspension, this shive will, when passing through the light beams 3 and 4, "cast a shadow" on each of the photodetectors 5 and 6 so that the light intensities received by these photo detectors are reduced. It will also be appreciated that the magnitude of this reduction in intensity and thus the magnitude of the corresponding amplitude reduction in the output signals of the photo detectors is a measure of the breadth or width of the shive in the directions perpendicular to the light beam 3 and the light beam 4, respectively, i.e., in two mutual perpendicular directions. Consequently, in this way the "breadth" as well as the "thickness" of the shive are measured, as the shive tends to orient itself in the pulp suspension flow in the measuring duct 1 with its longitudinal direction coinciding with the flow direction. It will also be appreciated that the duration of the intensity reduction and thus the duration of the amplitude reduction in the output signals of the two photo detectors 5 and 6 will be a measure of the length of the shive.

The output signals from the photo detectors 5 and 6 are supplied to a signal processing and display unit 7. In this unit the two output signals from the photo detectors 5 and 6 are combined to a combined signal, for instance in that the output signals from the photo detectors are added to each other, and this combined signal is then analyzed with respect to the temporary amplitude reductions occurring in the signal due to shives present in the pulp suspension flow. By determining the average amplitude of the combined signal over a given period of time it is for instance possible to determine the average content of shives in the quantity of pulp which has passed through the measuring duct 1 during said period of time.

According to the invention the light beams 3 and 4 consists of light having a wavelength within the range from 750 to 950 nm. Preferably one may use luminiscence diodes with the wavelength 930 nm as light sources for the light beams, as such luminiscence diodes are readily available on the market.

By using light within this infra-red wavelength range it is acheived that the measuring device is unsensitive to the type of pulp being examined, i.e., to the production process and the degree of bleaching of the pulp. This is not achieved when light having a wavelength outside of said wavelength range is used.

This is illustrated by the curves in the graphical presentation in FIG. 2, which show the transmission, i.e., the percentage ratio between the exit intensity and the incident intensity of a light beam, as a function of the wavelength of the light and for four different shives of different origins. The measurements, on which the curves in FIG. 2 are based, were carried out by passing a single shive of each type through the measuring duct in a water flow and without any fibers present and by measuring the transmission of the light beam at the passage of the shive through the illuminated section of the measuring duct with the use of light of different wavelengths within the range from 400 to 1000 nm. The shives being used had a cross-section dimension within the range from 150 × 150 $\mu$m to 200 × 200 $\mu$m, In FIG. 2 the transmission curve A was obtained for a shive from mechanical pulp, whereas the curve B was obtained for a shive from a CE-bleached pulp, curve C was obtained for a shive from unbleached pulp and the curve D was obtained for a shive from a CEH-bleached pulp.

As can be readily seen from the curves in FIG. 2, the different types of shives, i.e., shives from different types of pulp, affect the transmission, i.e., the intensity of the light beams leaving the measuring duct, substantially to the same extent, if the light being used has a wavelength within the range from 750 to 950 nm. For light having a wavelength outside this wavelength range, however, the different types of shives affect the intensity of the light beams to highly different extents, which means that very different measuring results would be obtained for different types of pulps when using light having a wavelength outside said wavelength range.

I claim:

1. A method for examining different types of pulp for shives therein, comprising the steps of flowing a suspension of the pulp through a measuring duct having transparent walls, directing at least one beam of light with a wavelength within the range from 750 to 950 nm through said measuring duct and the pulp suspension flow therein perpendicularly to the direction of the suspension flow, said light beam being comparatively thin in the direction of the suspension flow, measuring the intensity of said light beam after its passage through the measuring duct by means of a photo detector, and analyzing the output signal of said photo detector with respect to temporary reductions in its amplitude caused by the passage through said light beam of shives present in the pulp, said temporary reductions serving to indicate the presence of shives independent and insensitive to the type of pulp.

2. A device for examining different types of pulp for shives therein, comprising a measuring duct for passing a flow of a suspension of the pulp to be examined, said measuring duct having transparent walls, at least one light source located at one side of said measuring duct wherein said light source directs a beam of light having a wavelength within the range from 750 to 950 nm through the measuring duct perpendicularly to the direction of the suspension flow therein, a photo detector disposed on the opposite side of said measuring duct for receiving said light beam after its passage through the measuring duct and for producing an output signal representative of the intensity of said light beam, and signal processing means for analysing said signal with respect to temporary reductions in its amplitude to detect the presence of shives independent and insensitive to the type of pulp.

3. A device as claimed in claim 2, wherein said light source is a luminiscence diode having a wavelength of 930 nm.

* * * * *